US007973925B2

(12) United States Patent
Lipson et al.

(10) Patent No.: US 7,973,925 B2
(45) Date of Patent: Jul. 5, 2011

(54) APPARATUS FOR STABILIZING MECHANICAL, THERMAL, AND OPTICAL PROPERTIES AND FOR REDUCING THE FLUORESCENCE OF BIOLOGICAL SAMPLES FOR OPTICAL EVALUATION

(75) Inventors: Jan Lipson, Cupertino, CA (US); Jeff Bernhardt, Santa Cruz, CA (US); Daniel Petrasek, Los Angeles, CA (US); William Freeman, Castro Valley, CA (US); Joseph M. Lipson, Cupertino, CA (US); Robert P. McNamara, San Jose, CA (US)

(73) Assignee: C8 Medisensors Inc., San Jose, CA (US)

( * ) Notice: Subject to any disclaimer, the term of this patent is extended or adjusted under 35 U.S.C. 154(b) by 356 days.

(21) Appl. No.: 12/026,478

(22) Filed: Feb. 5, 2008

(65) Prior Publication Data
US 2008/0186471 A1 Aug. 7, 2008

Related U.S. Application Data

(60) Provisional application No. 60/888,487, filed on Feb. 6, 2007.

(51) Int. Cl.
*G01J 3/44* (2006.01)
(52) U.S. Cl. .................... 356/301; 356/338; 600/476
(58) Field of Classification Search .............. 356/36–38, 356/337–338, 342–343, 440, 244, 246, 301; 422/102, 104; 600/310
See application file for complete search history.

(56) References Cited

U.S. PATENT DOCUMENTS

| 3,508,830 | A | * | 4/1970 | Hecht et al. | 356/338 |
|---|---|---|---|---|---|
| 3,988,437 | A | | 10/1976 | Bradner | |
| 4,108,794 | A | | 8/1978 | Yonekubo | |
| 4,830,017 | A | * | 5/1989 | Perry et al. | 600/485 |
| 5,240,007 | A | * | 8/1993 | Pytel et al. | 600/485 |
| 5,719,700 | A | * | 2/1998 | Corcuff et al. | 359/368 |
| 6,066,505 | A | | 5/2000 | Cheng et al. | |
| 6,654,620 | B2 | * | 11/2003 | Wu et al. | 600/310 |
| 6,856,458 | B2 | | 2/2005 | Greenwald et al. | |
| 7,225,010 | B1 | * | 5/2007 | Zavislan | 600/407 |
| 7,299,079 | B2 | * | 11/2007 | Rebec et al. | 600/316 |
| 2004/0002162 | A1 | | 1/2004 | Leugers et al. | |
| 2004/0039271 | A1 | * | 2/2004 | Blank et al. | 600/322 |

(Continued)

OTHER PUBLICATIONS

Gillies et al., "Fluorescence Excitation Spectroscopy Provides Information About Human Skin in Vivo," The Journal of Investigative Dermatology, Oct. 2000, p. 704-707, vol. 115, No. 4.

(Continued)

*Primary Examiner* — Tarifur Chowdhury
*Assistant Examiner* — Michael LaPage
(74) *Attorney, Agent, or Firm* — Fenwick & West LLP (57) ABSTRACT

An apparatus is presented in which a sample can be accurately repositioned in a spectroscopic and/or imaging apparatus upon multiple insertions, and where the apparatus can be worn by living subjects for extended periods of time. The apparatus additionally reduces the temperature increase and stabilizes the temperature of the sample upon irradiation with an optical source of excitation. Additionally, the apparatus stabilizes the pressure and critical optical properties of the sample and its interface with the apparatus. Alternatively or additionally, the apparatus can be used to alter and/or substantially reduce fluorescence from targeted fluorophores in the sample.

4 Claims, 7 Drawing Sheets

U.S. PATENT DOCUMENTS

2006/0079792 A1     4/2006    Finburgh et al.
2008/0221457 A1*   9/2008    Zeng et al. .................... 600/477

OTHER PUBLICATIONS

PCT International Search Report and Written Opinion, PCT/US2008/053172, Jul. 16, 2008.

K. Giering et al., *Review of thermal properties of biological tissues*, Laser-Induced Interstitial Thermotherapy, 1995, pp. 45-60, SPIE Optical Engineering Press, U.S.A.

Valery V. Tuchin, *Optical Clearing of tissues and blood using the immersion method*, J. Phys. D: Appl. Phys., Jul. 22, 2005, pp. 2497-2518, vol. 38.

Valery V. Tuchin, *Optical Clearing of Tissues and Blood*, 2006, pp. 61-82 & 87-105, SPIE Optical Engineering Press, U.S.A.

Valery V. Tuchin et al., *Numerical technique for modeling of laser-induced hyperthermia*, Laser-Induced Interstitial Thermotherapy, 1995, pp. 100-111, SPIE Optical Engineering Press, U.S.A.

Chinese First Office Action, Chinese Application No. 200880003802.0, Jul. 9, 2010, 18 pages.

* cited by examiner

APPARATUS FOR STABILIZING MECHANICAL, THERMAL, AND OPTICAL PROPERTIES AND FOR REDUCING THE FLUORESCENCE OF BIOLOGICAL SAMPLES FOR OPTICAL EVALUATION

CROSS-REFERENCE TO RELATED APPLICATION(S)

This application claims priority under 35 U.S.C. §119(e) to U.S. Provisional Patent Application Ser. No. 60/888,487, "Apparatus for Stabilizing Mechanical, Thermal, and Optical Properties and for Reducing the Fluorescence of Biological Samples for Optical Evaluation," filed Feb. 6, 2007, the subject matter of which is incorporated herein by reference in its entirety.

BACKGROUND OF THE INVENTION

1. The Field of the Invention

This invention relates generally to stabilizing the position, temperature, and optical scattering characteristics of a biological sample undergoing optical evaluation.

2. Background and Relevant Art

Many forms of optical evaluation are being developed as noninvasive means of characterizing the chemistry and morphology of biological samples. In a number of applications it is desired to ascertain important properties of the tissue by spectroscopic analysis. For example, spectroscopy can be used to ascertain the concentration of an analyte of interest within the sample. In such cases, there may be variations in the chemical composition of the sample as a function of position (site to site variations). If the spectra of the chemicals which vary from site to site have some overlap with the spectrum of the analyte of interest, it is often difficult to obtain a calibration for the analyte concentration from multiple sites.

In addition, many important properties of the sample will change as a function of temperature. Examples include diffusion rates, vascular dilation, metabolic rates, and perspiration. A change in any of these properties can have significant effects on scattering and propagation of light through the material. In cases where lasers which deliver substantial power levels must be used to illuminate the sample, in order to obtain an adequate signal, the temperature increase caused by the laser radiation can interfere with the measurement. At sufficiently high powers the elevation of temperature caused by the laser can also damage or destroy proteins by denaturation, and cause a local burn to the skin of the subject.

In order to prevent excessive temperature excursions, it is useful to place the sample in contact with an optical window, the thermal conductivity of which is substantially higher than that of the sample. In such cases however, evaporation of volatile compounds such as water is impeded by the presence of the window. An illustrative example would be that of human skin where the deeper layers contain more water than the surface layers and when the evaporation from the surface is interrupted, moisture will diffuse into the outer layers and to the interface with the window. The progressive change of the moisture in these surface layers, and at the window interface, alters the scattering and reflection characteristics under optical illumination. The changing scattering and reflection characteristics may make it impossible to observe other changes that may be occurring on the same time scale. For example, if the concentration of some analyte in the skin is changing, the signal from spectroscopy for that analyte would be expected also to change, however, the changing scattering properties will also affect the size of the signal which is observed, and it can be exceptionally difficult to distinguish the two effects.

It is also observed that pressure on the sample can affect its optical properties, and fluids present in the sample can be physically moved by pressure. If the pressure is not fixed in time, the effects of changes in pressure can also be difficult to distinguish from changes in signal size associated with fluctuations in what is desired to be measured.

Finally, it is also the case that fluorescence from fluorophores present in the sample (autofluorescence), can interfere with certain forms of spectroscopic evaluation. For example, melanin is a strong fluorophore in human skin at excitation wavelengths in the visible range extending to the near IR range. If it is desired to obtain the Raman spectrum of an analyte of interest in human skin, the fluorescence induced by the laser, which is used to irradiate the sample, is usually the principle source of random noise in the measurement. In other cases, the fluorescence of one analyte is of interest, but the fluorescence of a second chemical which is also present in the sample is not of interest and is a source of unwanted interference. If one does not change the position of the sample during the course of the experiment, the analysis is generally simpler. Typically, the fluorescence will decay monotonically over time. This phenomenon is called photo-bleaching. If this process is interrupted by moving to a new spot on the sample, then the decay will start over again, thus complicating the analysis.

SUMMARY OF THE INVENTION

These and other limitations are addressed by the present invention in which an apparatus stabilizes the optical, thermal, and mechanical interface between a spectroscopic and/or imaging system and a biological sample. The following properties can be achieved simultaneously, or in any combination:

a. The same site can be targeted for measurement even if the interval between measurements is long, and even if the sample is withdrawn and later returned to the apparatus. For example, a human subject could depart and return to the apparatus and the measurement could nevertheless be made on the identical site.
b. Temperature rises due to laser irradiation can be substantially reduced.
c. The scattering properties of the sample and the reflection properties at an interface between the sample and an optical window can be stabilized for long intervals.
d. The pressure on the sample can be held substantially constant.
e. Unwanted fluorescence from targeted fluorophores can be substantially reduced.

The apparatus may be considered to be comprised of two major assemblies. The spectroscopic and/or imaging system contains the excitation source and viewing equipment. The sample apparatus is attached to the sample and can be but is not necessarily physically separate from the spectroscopic and/or imaging system.

The sample apparatus may contain an optical window which is substantially transparent to both the excitation wavelength and to any wavelengths which the sample emits upon excitation and which are desired to be observed. This window is attached to the sample by either temporary or permanent means. In one embodiment, for example, it is mounted in and retained by a frame of appropriate material which is attached to a limb of a living subject by straps, the window being in contact with the skin.

To stabilize the optical properties of the sample, an appropriate fluid, gel, adhesive or elastomer is introduced at the surface of the sample. If a window is employed, the fluid, gel, adhesive or elastomer is introduced at the interface between the window and the sample. By suitably choosing the composition of the fluid, gel, adhesive or elastomer, selective suppression of fluorescence can be obtained from fluorophores that are accessible by diffusion to the fluid.

Positional reproducibility and stability is achieved through suitable mechanical registration between the spectroscopic and/or imaging system and the sample apparatus. Each time the sample is returned to the spectroscopic and/or imaging system, the registration of the sample apparatus to the spectroscopic and/or imaging system assures that the sample is in appreciably the same position with respect to the excitation beam and the viewing optics. In addition, unwanted motion between parts of the sample apparatus and the sample can be suppressed by using a material on the surface of the sample apparatus that has large coefficient of friction with respect to the sample, such that the retention forces exerted by straps, for example, produces sufficient static friction to suppress relative motion. Alternatively, adhesive can be used where feasible.

A window may be employed to provide thermal stabilization. The window material should be chosen such that its thermal conductivity is much greater than that of the sample. It is possible, for example, to choose window materials whose thermal conductivity is greater than fifty (50) times that of human skin. A good thermal connection between the window and the spectroscopic and/or imaging system is also useful. The presence of fluid at the interface between the window and the sample also promotes thermal conduction. For example, the thermal conductivity of water, about 0.45 W/m-° K, is approximately 20 times better than air.

The pressure on the sample can be substantially constant, and can be controlled for example by adjusting the tension in straps which are used to press a window in its frame against the sample. Note that in general there will be a correlation between the strap pressure and the friction between the test subject or sample and the apparatus, which keeps the apparatus from moving.

Particularly advantageous is that in some embodiments, the apparatus containing the window can be worn for extended periods of time by live subjects without interfering with their normal activities, and without substantially altering their appearance.

Additional features and advantages of the invention will be set forth in the description, which follows, and in part will be obvious from the description, or may be learned by the practice of the invention.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 3a is representative of the prior art.

DETAILED DESCRIPTION OF THE PREFERRED EMBODIMENTS

Figure 1:
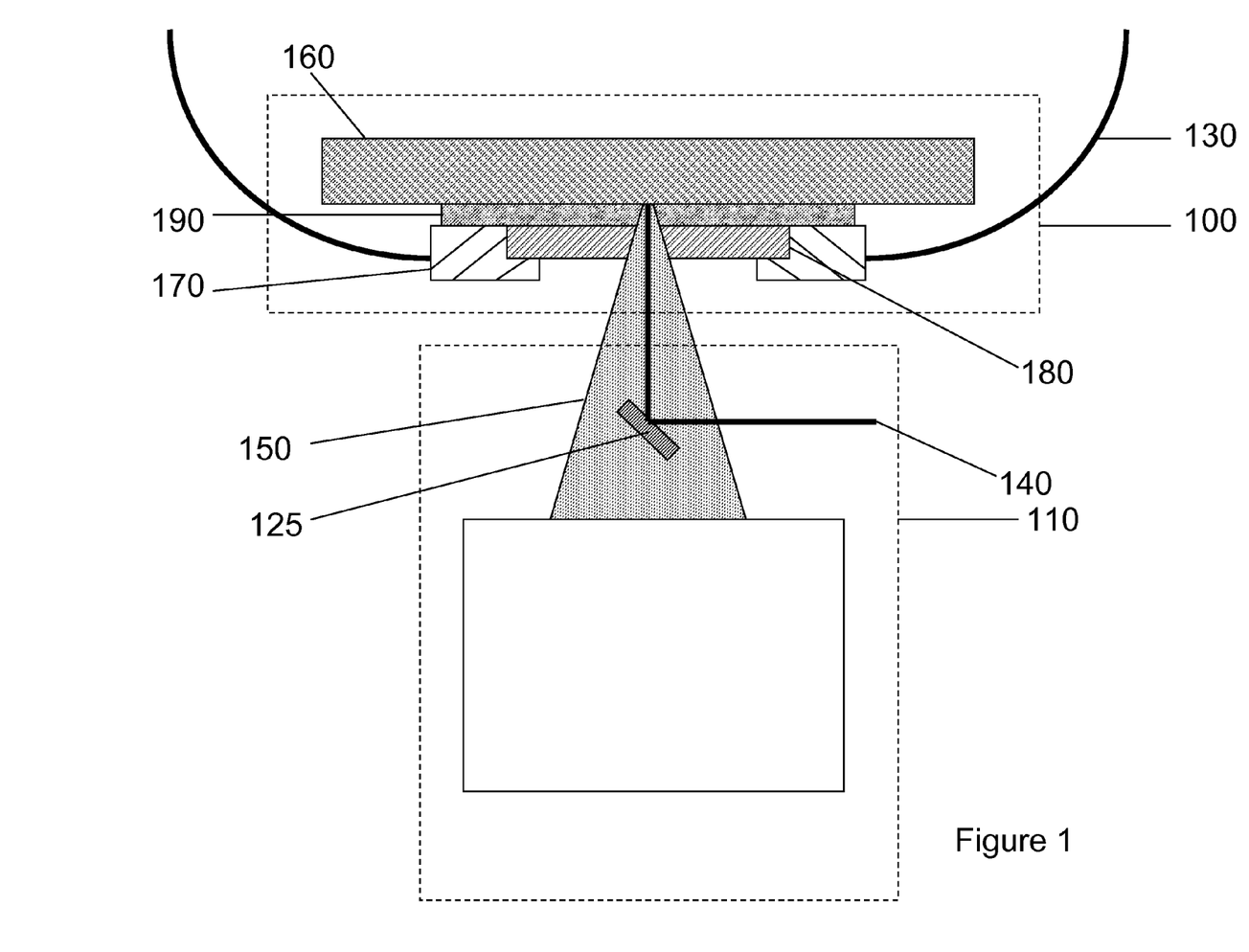
FIG. 1 is a cross-section diagram of the apparatus identifying the functions of the spectroscopic and/or imaging system and of the sample apparatus, in accordance with an embodiment.

FIG. 1 is a cross-section diagram of the apparatus, in accordance with an embodiment. The apparatus is comprised of the sample apparatus 100, which includes a strap 130 disposed on either side to secure the sample apparatus 100 to the test subject or sample 160, and the spectroscopic and/or imaging system 110. The spectroscopic and/or imaging system 110 comprises the light excitation beam 140 which arises from a source within the spectroscopic and/or imaging system 110, a mirror 125 that is one means of introducing the beam 140 to the sample 160, and appropriate collection optics (not shown) to capture and guide the scattered radiation 150 from the sample 160 that passes from the sample apparatus 100 to the spectroscopic and/or imaging system 110. The excitation beam 140 passes between the spectroscopic and/or imaging system 110 and the sample apparatus 100. In FIG. 1, the sample apparatus 100 is comprised of an optical window 180 and frame 170 which retains the optical window 180, a fluid, gel, adhesive, or optically transparent elastomer 190 introduced between the optical window 180 and the sample 160, and a means of attaching the optical window 180 within the frame 170 to the sample 160, which in one embodiment are straps 130. In some embodiments of the foregoing, as will be explained in the following, any one of items 170, 190, 180, or 130 may be omitted, either singularly or in combinations. For example, the window 180 may be a simple aperture.

Figure 2A:
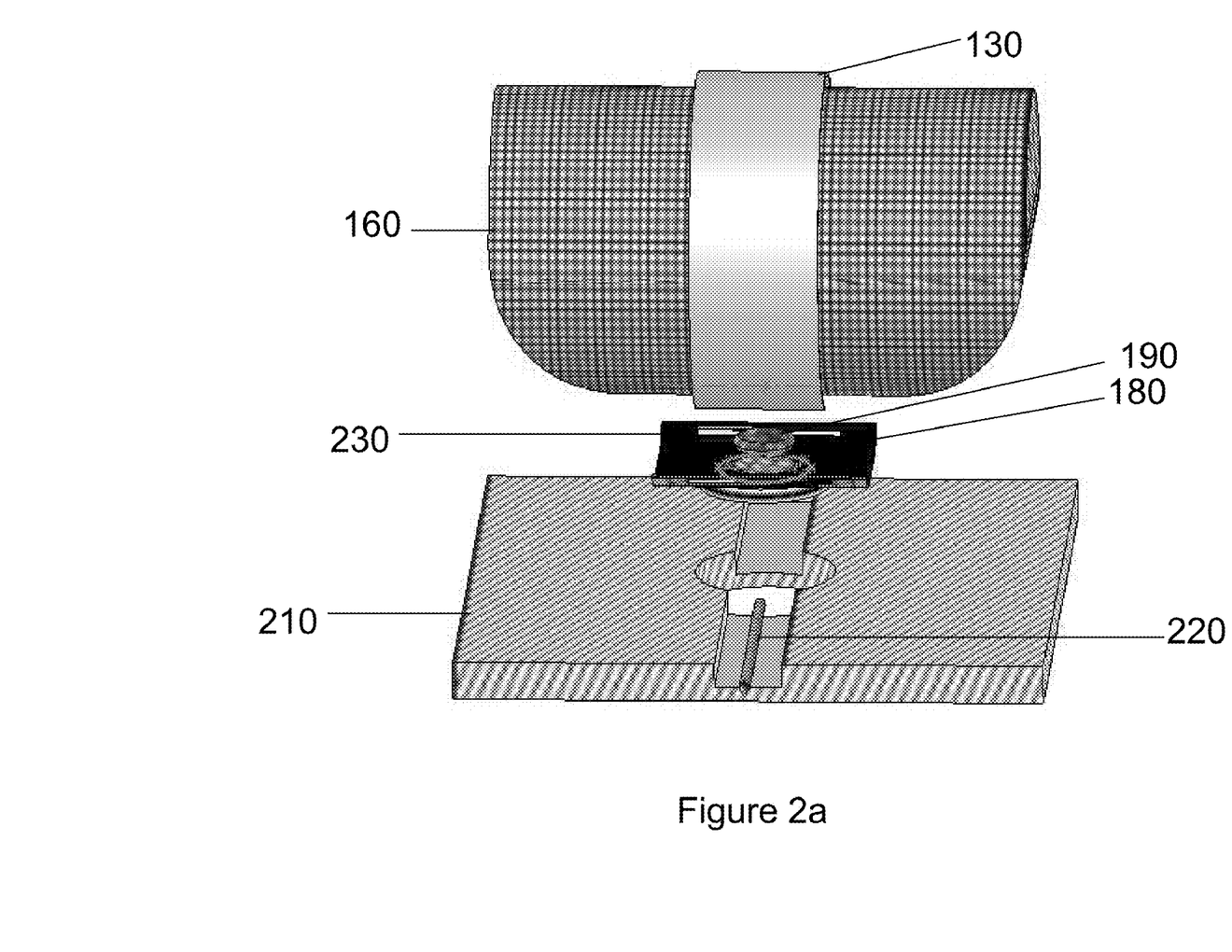
FIG. 2a shows an exploded view of the sample apparatus and the means of attaching it both to the sample and to the spectroscopic and/or imaging system in accordance with an embodiment.
Figure 2B:
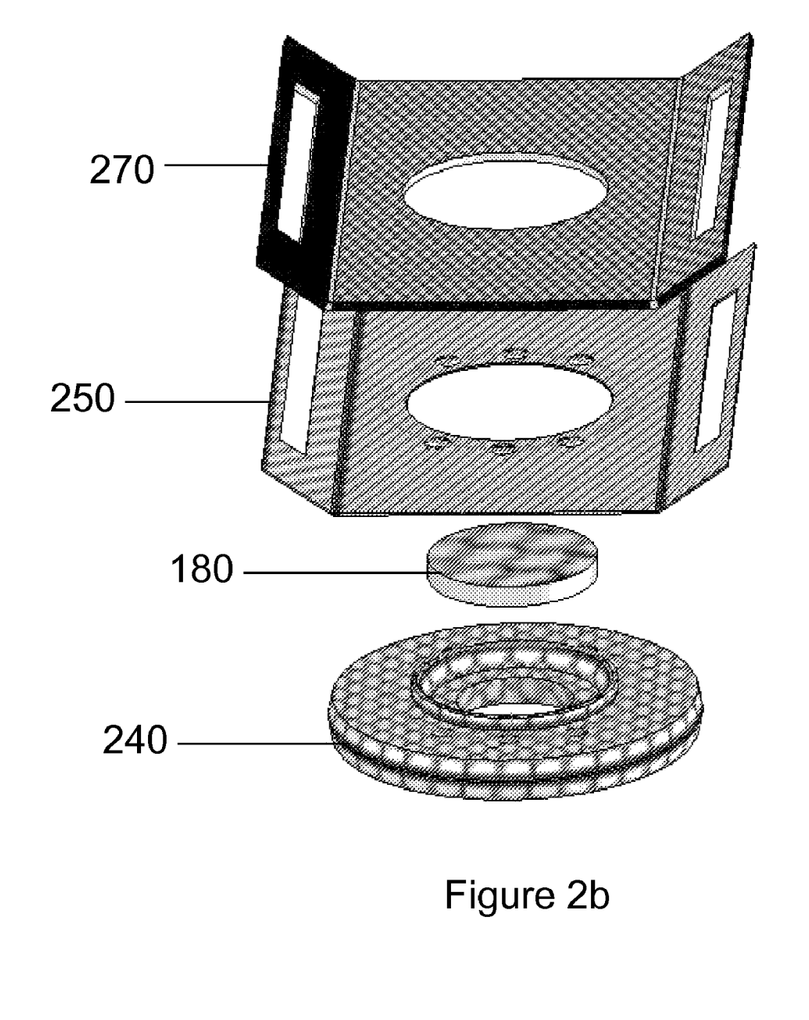
FIG. 2b shows an exploded view of a subassembly that contains an optical window.

FIG. 2a shows an exploded view of one preferred mechanical reference feature of the apparatus used for reproducibly securing the sample apparatus 100 to the spectroscopic and/or imaging system 110. The intention of the design of FIG. 2a is that the sample apparatus 100 can be withdrawn from the spectroscopic and/or imaging system 110 any number of times but that each time the sample apparatus 100 is engaged, the excitation beam 140 will illuminate appreciably the same location on the sample 160 to a degree of precision of, for example, less than 5 mm. This is particular useful for extended tests on live human subjects because the subject may be obliged to take occasional breaks. In FIG. 2a, the spectroscopic and/or imaging system 110 includes a plate 210. The excitation beam 140 and scattered radiation 150 will pass through the aperture shown in plate 210. Item 230 is a sub-assembly, which has rectangular apertures for attachment of straps 130. FIG. 2b is a detailed exploded view of sub-assembly 230. Item 240 in FIG. 2b is a retainer for the window 180. Retractable spring loaded pin 220 of FIG. 2a is intended to contact the periphery of window retainer 240 when the window retainer 240 is inserted into the aperture of plate 210. Pin 220 is intended to exert a force upon window retainer 240 such that it will register firmly in the aperture of plate 210. Referring to window retainer 240 in FIG. 2b, it is advantageous to slope the edge outwards and then inwards from bottom to top as is represented in the figure. As window retainer 240 is inserted, the slope will cause pin 220 to retract, but upon complete insertion, the pin 220 will register on the top part of the periphery of window retainer 240, which is sloped in the opposite direction. Upon complete insertion, a component of the pin force will therefore exist in the downwards direction which will help hold window retainer 240 securely. In a particularly preferred embodiment, the pin 220 is retractable by translation away from window retainer 240 when it is desired to release the sample apparatus 100 from the spectroscopic and/or imaging system 110. This assures that it will not be necessary to apply excessive force upon release which could disturb the alignment of parts of the sample apparatus 100 to the sample 160.

A further precaution against relative movement of the sample 160 and straps 130 is shown in FIG. 2b. Item 250 is a part which provides a means of attaching possible straps 130 and the window retainer 240. It is advantageously formed from material with moderate flexibility and good wear characteristics such as sheet metal. In some embodiments, item 270 is a coating or a separate insert of a material with high coefficient of friction with respect to the sample 160. It can advantageously be chosen to be fabricated from natural or synthetic rubber or can be applied as a coating as with rubber cement, for example. In one embodiment, at least some material in contact with the biological sample 160 has a coefficient of friction with respect to the biological sample 160 greater than 0.1.

It will be recognized that a great variety of methods and mechanisms can be used to assure reproducible mechanical registration of the sample apparatus 100 to the spectroscopic and/or imaging system 110. One example would be to use two (2) or more pins 220 any or all of which can be retractable. In fact, the embodiment presented in FIG. 2a, has two other fixed pins not shown in the diagram for clarity. Thus, when in place, the window retainer 240 is held at three points, orienting it firmly in the desired plane. A circular snap ring could be used in the aperture of plate 210. Window retainer 240 could be omitted and the window 180 itself could be inserted into the aperture in plate 210. Neither the aperture in plate 210 nor the window 180 or the window retainer 240 need be circular. Window 180 could be cemented to the sample 160 with an appropriate adhesive. In such a case the window retainer 240, strap attach 250, high friction insert or coating 270, and straps 130 could be omitted. Alternatively, the window retainer 240 could be cemented to the sample 160 in which case the strap attach 250, the high friction insert or coating 270, and straps 130 could be omitted. These and any means which derive from them, of obtaining reproducible and stable mechanical registration of the sample 160 and spectroscopic and/or imaging system 110 are considered to be within the scope of the invention.

The pressure on the sample 160 may affect its physical, optical, and chemical properties. It is desirable therefore that the pressure be fixed. It is also important for living subjects that the pressure not be excessive so that the apparatus can be worn for extended periods without harm. The pressure in this case can be regulated by adjusting the tension in straps 130 in FIG. 1. The adjustment can be made to achieve a precise pressure if a pressure sensor is incorporated in the sample apparatus 100. The embodiment could also include an automated tension adjustment, using closed-loop control, to respond to pressure variations resulting from changes in tissue hydration or other causes. Alternatively, the tension can be adjusted for comfort.

An optical window 180 can be employed for thermal reasons. In some cases, it is desired to apply high power densities of optical radiation to the sample 160. An example would be for Raman spectroscopy, where due to the weakness of the Raman effect, a large amount of excitation power may be necessary to obtain adequate signal. It is often also desirable that the excitation beam 140 not perturb the temperature of the sample 160. For example, in making a noninvasive measurement of the concentration of some analyte in live human skin, it is desirable not to perturb parameters that may affect the concentration of that analyte. Human or animal tissue will respond to heating by increasing blood perfusion, and cell metabolism will also be affected. Perspiration and modified diffusion rates are also possible. Of course, in more extreme cases, proteins may denature, and burning of tissue may transpire. Human tissue is observed to have very low thermal conductivity (<0.6 W/m° K), as is discussed in "Laser Induced Interstitial Thermotherapy," SPIE Optical Engineering Press, ISBN 0-8194-1859-5, G. Muller, and A. Rogan, 1995, pgs. 49-60. In consequence, beams of even moderate power may cause large temperature changes (see for instance pg. 109-111 in Muller referred to above). The thermal conductivity of the optical window 180 can be much higher than that of the sample 160. For example, the thermal conductivity of sapphire is 42 W/m° K, about 70 times better than skin, as a whole, and around 160 times better than air. In consequence, if the window 180 is attached to the sample 160, it can greatly mitigate the expected temperature rise.

A distinct set of benefits can be obtained when a window 180 is used in conjunction with a fluid, gel, adhesive or elastomer 190. In that instance, the presence of the window 180 physically stabilizes the thickness of the layer of fluid, gel, adhesive or elastomer 190, and also impedes any evaporation. In another embodiment, the window 180 comprises the same material as the fluid, gel, adhesive or elastomer 190. In one example, the fluid, gel, adhesive or elastomer 190 comprises a silicone compound.

When employing an optical window 180 it can be important to stabilize the optical interface between the sample 160 and the window 180, and also layers of the sample 160 near the surface. One mechanism of instability is the evolution of moisture from some samples such as human skin. The dermis has a larger water content than the epidermis and water normally diffuses from the dermis to the epidermis top layer (stratum corneum) and is lost by evaporation. The presence of the window 180 impedes evaporation, so the water will accumulate in the epidermis and at the interface between the skin and the window 180. The optical properties such as scattering of both the epidermis and the interface between the window 180 and the skin will thereby change substantially. The changing optical properties will change both the scattering of the excitation beam 140 and the scattering of the radiation 150 which is produced by that excitation. The intensity profile of the excitation beam 140 in the tissue will therefore be modified, as will the spatial pattern of the radiation 150 emitted by the sample 160. The efficiency with which spectral lines of interest are transferred to the spectroscopic and/or imaging system 110 will be modified accordingly. The time variance of the intensity of these spectral lines caused only by the changes in optical properties is subject then to confusion with possible variations in analyte concentration that might also have caused variations on similar time scales.

Figure 3A:
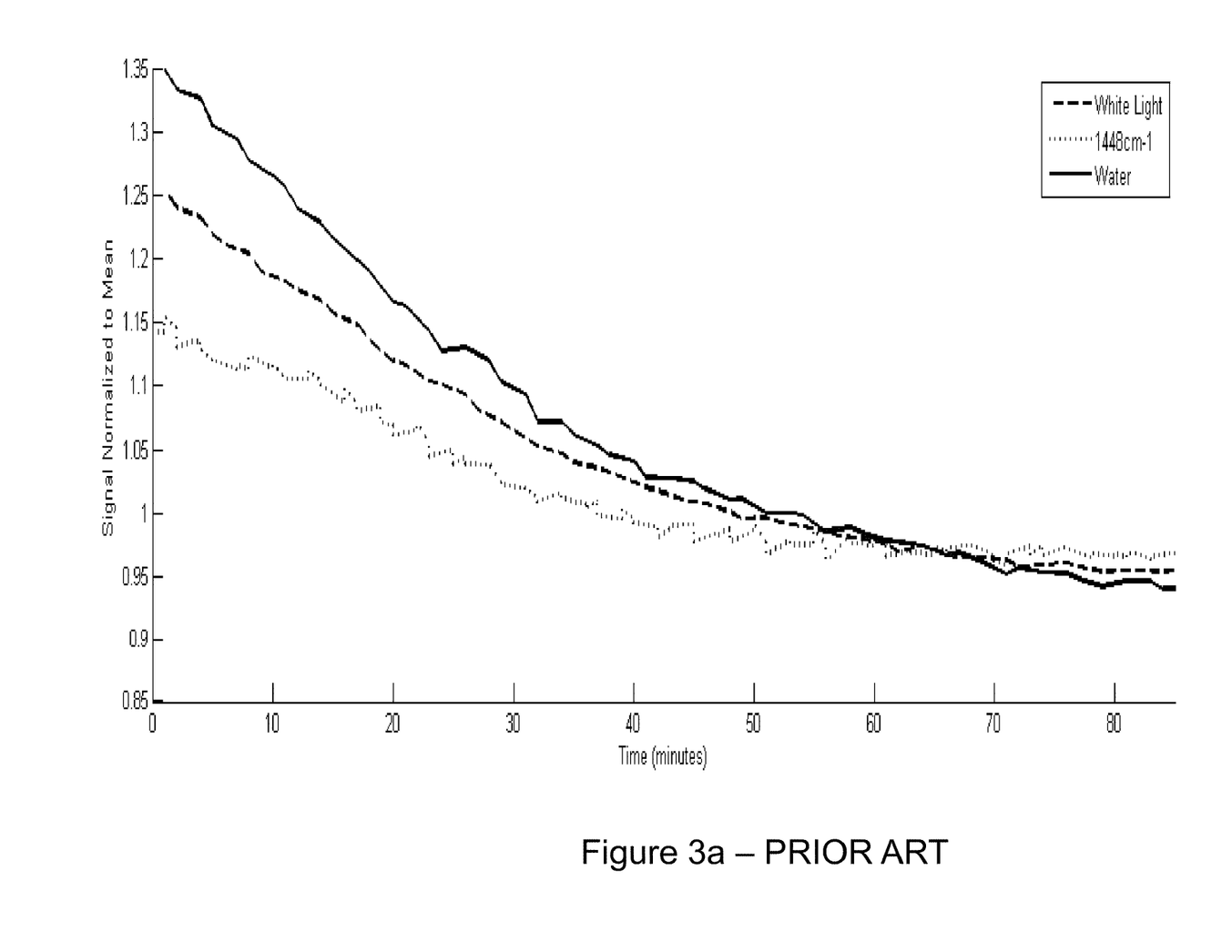
FIG. 3a is a plot of white light scattering amplitude, water signal, and total integrated counts in the 1448 cm$^{-1}$ Raman line ($CH_2$ scissoring mode) versus time for human skin in contact with a window but with no fluid added at the interface.

The state of the prior art with respect to time variation of important spectral measurements is presented in FIG. 3a. The data presented are from human skin. Three distinct excitation sources were utilized. One operated substantially at 830 nm wavelength. A second source operated at 670 nm. The third source consisted of white light which had spectral content within the useful bandwidth of the spectrometer (about 845 to 960 nm). Time profiles were obtained by taking multiple measurements using each of these sources. The output of the excitation at 830 and 670 nm is a broadband fluorescence with Raman lines of various chemicals superimposed. The largest Raman line observed in human skin, which is observed with the 830 nm laser excitation, is at about 1448 $cm^{-1}$ and represents $CH_2$ scissoring modes. The detected signal integrated over the range of wavelengths in which this line is observed is presented in FIG. 3a. Also presented is the white light scattering at a detected wavelength of about 860 nm. Lastly, it is possible to observe the Raman line of water at about 3400 $cm^{-1}$ in the 670 nm spectrum. The total amount of water calculated from the integrated signal associated with this line is presented. All the presented signals are normalized with respect to their respective means over time. It is observed that all three of the presented measurements in FIG. 3a decrease substantially. This is so, even though no deliberate change in the sample had been introduced. It is clear from the foregoing that since these changes are not associated with changes in the composition of the sample, they may be highly undesirable when attempting to assess compositional changes. This is particularly so when the expected change in spectrum due to the change in composition desired to be determined is expected to be small, as for example, for a noninvasive Raman measurement of glucose.

Figure 3B:
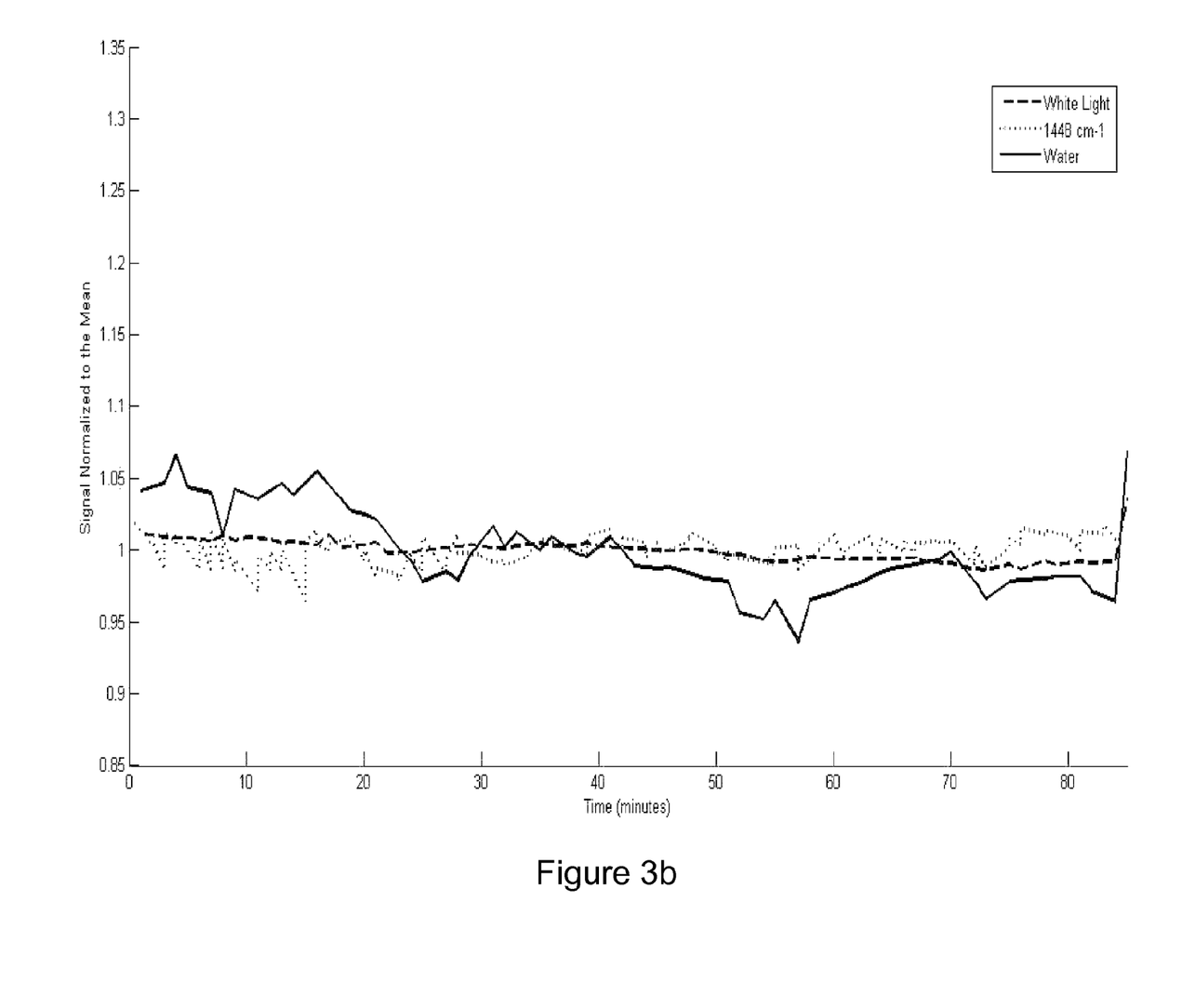
FIG. 3b is a similar plot when water has been added at the interface between the window and the human skin, in accordance with an embodiment of the invention.

In FIG. 3b, signals of the same type as in FIG. 3a are presented, but the data in FIG. 3b were taken with a water layer deliberately introduced between the skin and the optical window 180. For comparison purposes, the data of FIGS. 3a and 3b are plotted on the same scales. It is obvious that all three major measures have been stabilized over time by a very great degree due to the presence of externally added water at the skin-window interface. The reduction can be decisive in finding the time-varying concentrations of relevant analytes by spectroscopy. The mechanism for the stabilization is that the equilibrium distribution of water at the interface between skin and window 180 is obtained very quickly and the outer layers of the epidermis also reach saturation very quickly. It is also seen that the stabilization is persistent. It has been observed to work for at least three (3) hours, which is the longest measurement made by the inventors, up to the date of this writing. The window 180 prevents evaporation and the water must diffuse laterally to the window edge before it can be lost by evaporation. This process is very slow.

It is possible to obtain considerable stabilization through the use of other fluids besides water. For instance, white light scattering and the large Raman line at 1448 $cm^{-1}$ are observed to be stabilized by low viscosity microscope immersion oil (Richard Allan Scientific, M2000). Water may not be stabilized by agents which can absorb water or by agents which affect the osmotic balance in the tissue. In one embodiment, the fluid comprises an oil having a vapor pressure at room temperature less than 50% of a vapor pressure of water at room temperature.

The foregoing also leads to conclusions concerning the requirements of the optical window 180 to be used. An optical window 180 will exhibit some reflectivity of light at its two interfaces. Multiple reflections between these interfaces produce a transmission characteristic of a Fabry-Perot etalon. If the reflectivity at one or both interfaces changes with time, the etalon will have a periodic transmission function whose amplitude may vary. This can be confusing when attempting to use the time-varying spectra to assess variations in analyte concentration over time.

In a particularly preferred embodiment, sapphire or diamond is selected for the window material because of their high thermal conductivity. If both the excitation and the observed spectrum are at wavelengths>1000 nm, a silicon window 180 can also be exceptionally advantageous. For excitation and observation in the mid-IR, zinc selenide is also a good choice. One surface of the window 180 has an interface to air. This surface is the side of the window 180 opposite from the biological sample 160. This surface should be anti-reflection coated to have a reflectivity<0.5% over the spectral range of the spectra being observed, in one embodiment. The second interface will be to the chosen fluid, gel, adhesive, or elastomer 190. This surface should have a second anti-reflection coating in one embodiment which is also designed to have a reflectivity<0.5% over the relevant spectral range, but this second coating will in general not be identical to that at the air interface because the indices of refraction of the materials at the two interfaces are not the same. In one embodiment, the index of refraction of the fluid, gel, adhesive, or elastomer 190 and the index of refraction of the window 180 differ by less than 0.5. In one implementation, the window 180 has an antireflection coating on the side nearest the biological sample 160 such that the reflection between the window 180 and the fluid, gel, adhesive, or elastomer 190 is less than 1%.

In a second preferred embodiment, magnesium fluoride can be chosen for the window 180. Although its thermal conductivity is lower than that of sapphire or diamond, the index of this material already closely matches that of water, so if water is used as the fluid, no coating is required on that side. Indeed it is found experimentally that the reflectivity is sufficiently low at this water interface that no coating is required on the air side of the magnesium fluoride window 180. That is because the amplitude of the periodic transmission function of a Fabry-Perot etalon is proportional to the geometric mean of the two reflectivities, so if one is sufficiently small the other can be larger.

In the prior art, a fluid that is applied to the sample was observed to be capable of altering and preferentially reducing the optical scattering of the sample. This phenomenon is referred to as optical clearing and has been extensively discussed (see, "Optical Clearing of Tissues and Blood," SPIE Press, ISBN 0-8194-6006-0, V. V. Tuchin, 2006).

Figure 4A:
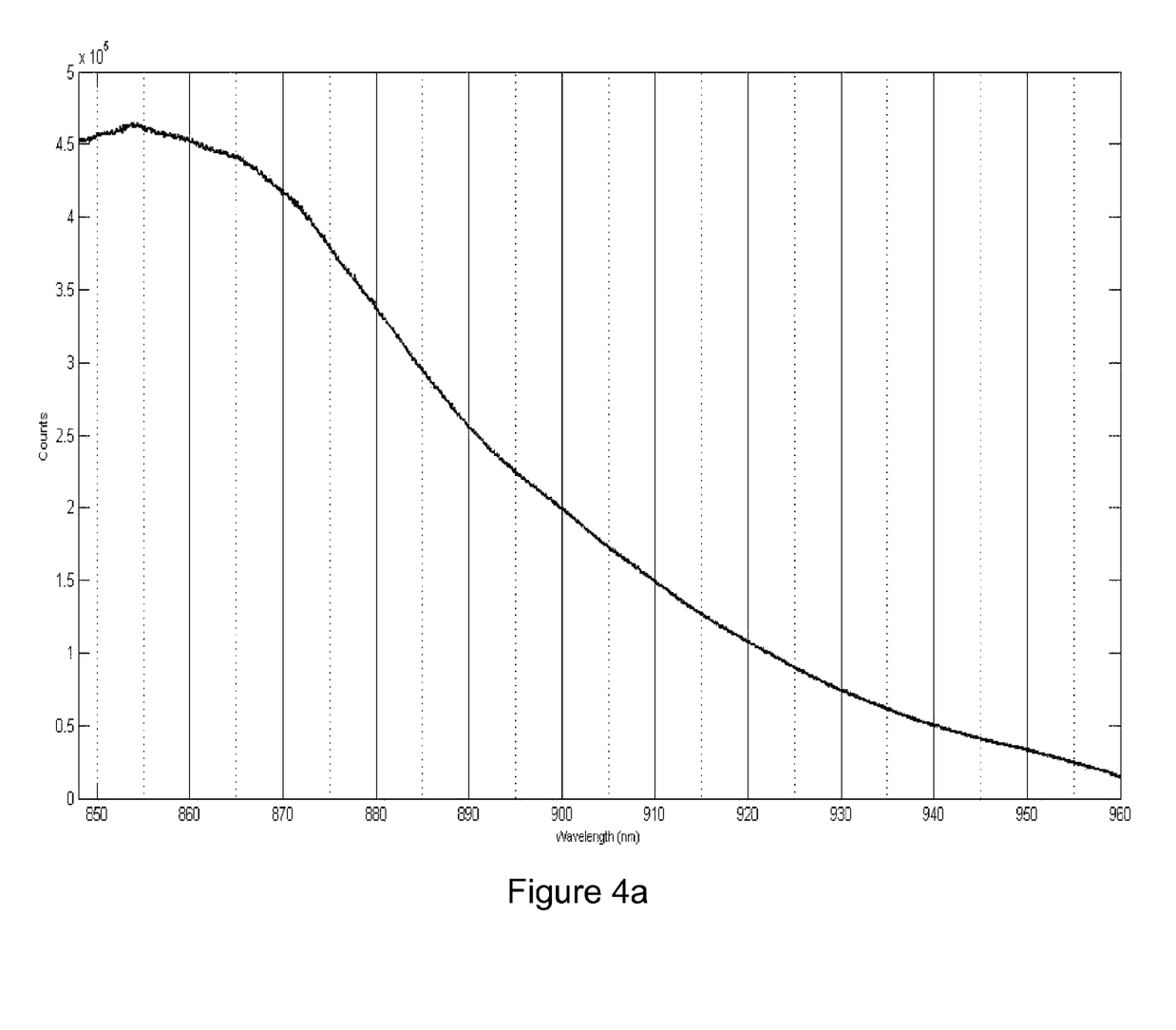
FIG. 4a is a spectrum of human skin with 670 nm laser excitation with the skin in contact with a window but with no fluid added at the interface, and is representative of the prior art.
Figure 4B:
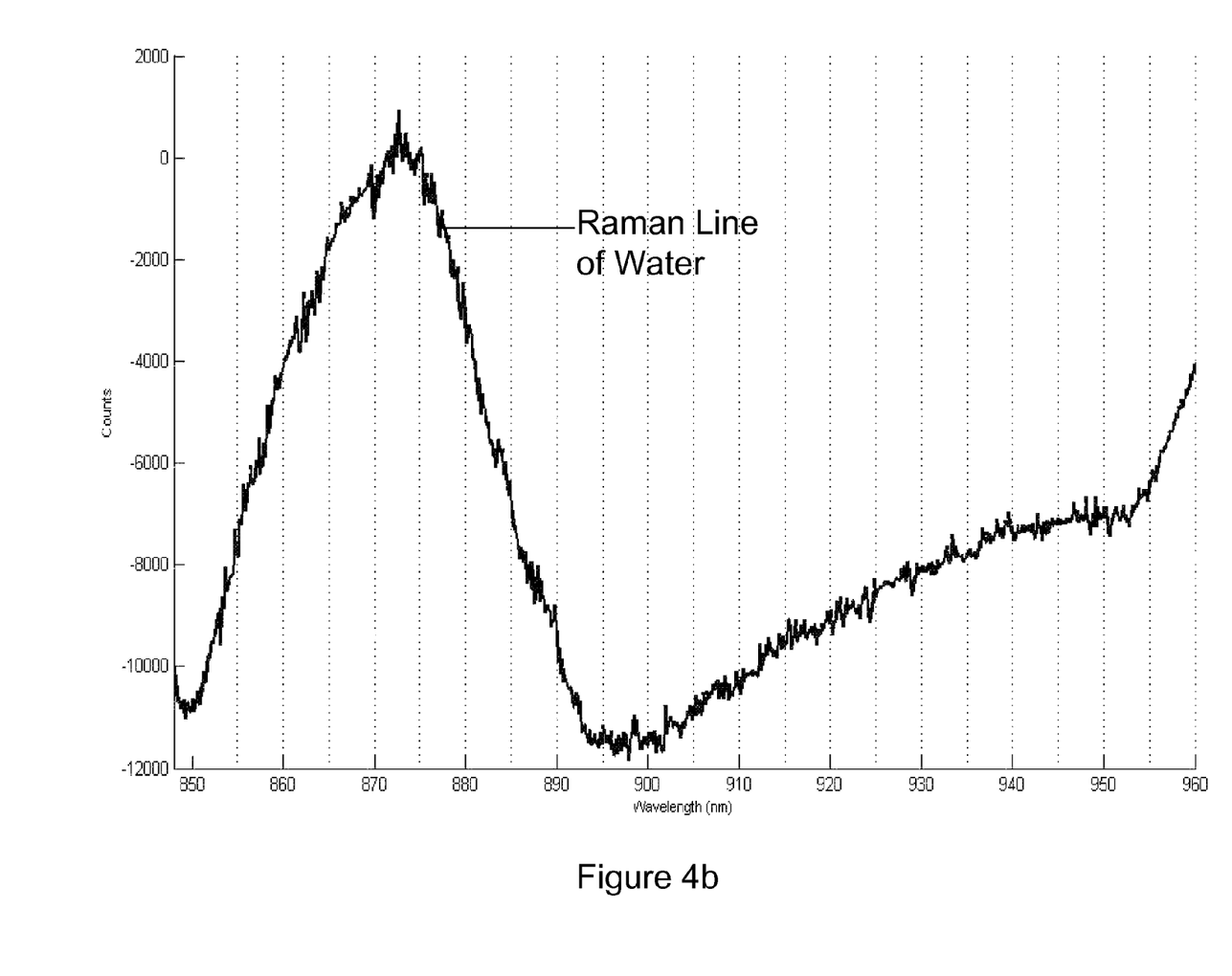
FIG. 4b is a similar spectrum but with a preparation of microscope immersion oil added at the interface between the optical window and the sample, in accordance with an embodiment of the invention.

It has now been found by the inventors that certain fluids may profoundly affect the fluorescence of biological samples. In particular, fluorescence from human skin has been suppressed by more than two orders of magnitude at an excitation wavelength of 670 nm. In FIG. 4a, the spectrum of human skin from excitation by 670 nm is presented at wavelengths from 848 to 960 nm. No fluid was added between the skin and optical window 180. It is observed that the peak signal value is about 450,000 counts. There is a Raman line of water at about 3400 $cm^{-1}$ which for excitation at 670 nm produces a peak in the neighborhood of 872 nm. It is not readily observed in FIG. 4a as the fluorescence signal dominates in magnitude. In FIG. 4b, relative counts (scattered signal from the sample minus a background taken with no sample) are again presented for 670 nm excitation; but microscope immersion oil (Richard Allan Scientific, M2000) has been introduced between the human skin and the optical window 180. So great was the suppression of fluorescence that the Raman line of water is now observed without any impairment.

Fluorescence is often the largest source of random noise in spectroscopy of biological samples. In particular, the variance of the fluorescence counts is very often the limiting random noise in Raman spectroscopy of biological samples. In fluorescence spectroscopy, the fluorescence from some chemicals can greatly interfere with the observation of fluorescence from the desired chemical. Therefore, a means of suppressing fluorescence from targeted chemicals is exceptionally valuable. In human skin, the fluorescence observed at an excitation of 670 nm arises substantially from melanin which is found in high concentrations in the pigmentation layer of the skin. It is therefore found that applying the oil in contact with the biological sample 160 has the effect of deactivation or quenching of this fluorescence by binding to the targeted source of the fluorescence in the skin, thus reducing the fluorescence yield. The oil used in the experiment was chosen to be non-toxic. Chemicals similar in structure are likely to have similar suppressive affects on this fluorescence. The principle components of the oil employed were mineral oil and Terphenyl. In various implementations, fluid or gel comprising Terphenyl, hydrogenated Terphenyls, or mineral oil can also be used. It should be clear from the foregoing that for purposes of altering fluorescence of the sample 160 with an appropriate fluid or gel, the presence of the window 180 and the other components in the sample apparatus 100 are not essential. The fluid or gel however is also useful when employing an optical window 180 to stabilize the optical interface, therefore the combination is very advantageous. The window 180 is useful in preventing any volatile components in the fluid from evaporating. Hence, the combination is advantageous on multiple grounds.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents.

The invention claimed is:

1. A method for reducing melanin fluorescence from a human tissue sample illuminated by optical radiation, the method comprising:
    placing an optical window in contact with the human tissue sample, the optical window being substantially transparent to the optical radiation and which is substantially transparent to light that is scattered from the human tissue sample;
    illuminating the human tissue sample with the optical radiation;
    detecting a first Raman scattering signal from the human tissue sample, the first Raman scattering signal comprising a first melanin fluorescence signal;
    interposing a fluid, gel, adhesive or elastomer between and in contact with both the optical window and the human tissue sample, the fluid, gel, adhesive or elastomer comprising a substance that chemically binds to melanin in the human tissue sample thereby reducing a melanin fluorescence yield from the melanin; and
    detecting a second Raman scattering signal from the human tissue sample, the second Raman scattering signal comprising a second melanin fluorescence signal, wherein the second melanin fluorescence signal is suppressed relative to the first melanin fluorescence signal.

2. The method of claim 1, wherein the fluid, gel, adhesive or elastomer contains Terphenyls or hydrogenated Terphenyls.

3. The method of claim 1, wherein the fluid, gel, adhesive or elastomer contains mineral oil.

4. The method of claim 1, wherein the fluid, gel, adhesive or elastomer is substantially transparent to the optical radiation and is substantially transparent to radiation scattered from the human tissue sample.

* * * * *